«12» United States Patent [19]
Matsushima et al.

[11] Patent Number: 5,646,117
[45] Date of Patent: Jul. 8, 1997

[54] THERAPEUTIC AGENT FOR TREATING WOUNDS USING MONOCYTE CHEMOTACTIC AND ACTIVATING FACTOR

[75] Inventors: Kouji Matsushima, Kanazawa; Masanobu Naruto, Kamakura, both of Japan

[73] Assignee: Toray Industries, Inc., Tokyo, Japan

[21] Appl. No.: 433,519

[22] PCT Filed: Sep. 13, 1994

[86] PCT No.: PCT/JP94/01512

§ 371 Date: Jul. 12, 1995

§ 102(e) Date: Jul. 12, 1995

[87] PCT Pub. No.: WO95/07710

PCT Pub. Date: Mar. 23, 1995

[30] Foreign Application Priority Data

Sep. 13, 1993 [JP] Japan .................. 5-227385

[51] Int. Cl.$^6$ .................................. A61K 38/19
[52] U.S. Cl. .................. 514/12; 424/85.1; 424/85.2; 514/21; 530/351; 530/324
[58] Field of Search ............... 514/12, 21; 424/85.2, 424/85.1; 530/324, 351

[56] References Cited

U.S. PATENT DOCUMENTS 5,202,118  4/1993  Gillis et al. ................... 424/85.2

FOREIGN PATENT DOCUMENTS 9007863  7/1990  WIPO.
9220372  11/1992  WIPO.

OTHER PUBLICATIONS

Robinson et al. PNAS USA, 86, 1850–1854 (1989).

*Primary Examiner*—Howard E. Schain
*Attorney, Agent, or Firm*—Birch, Stewart, Kolasch & Birch, LLP

[57] ABSTRACT

A therapeutic agent for treating wounds having properties and actions different from those of growth factors and proteins inducing growth factors, which have strong therapeutic effect is disclosed. The therapeutic agent for treating wounds according to the present invention comprises monocyte chemotactic and activating factor or a variation thereof having a monocyte-attracting property or a derivative of said monocyte chemotactic and activating factor or said variation thereof.

10 Claims, 4 Drawing Sheets

THERAPEUTIC AGENT FOR TREATING WOUNDS USING MONOCYTE CHEMOTACTIC AND ACTIVATING FACTOR

TECHNICAL FIELD

The present invention relates to a therapeutic agent for treating wounds.

BACKGROUND ART

Several factors having chemotactic properties to monocytes are known. Among these, monocyte chemotactic and activating factor (hereinafter referred to as "MCAF") also known as MCP-1 (monocyte chemoattractant protein-1) or GDCF (glioma-derived monocyte chemotactic factor), is a protein consisting of 76 amino acids, which has 4 cysteine residues. It is known that this protein has a strong chemotactic activity to monocytes and a strong monocyte-activating property.

Identification and gene cloning of MCAF, MCP-1 and GDCF are described in the following references:

1) K. Matsushima et al., J. Exp. Med., 169, 1485–1490, 1989;

2) Y. Furutani et al., Biochem. Biophys. Res. Commun., 159, 249–255, 1989;

3) E. A. Robinson et al., Proc. Natl. Acad. Sci. USA, 86, 1850–1854, 1989; and

4) T. Yoshimura et al., FEBS Letters, 244, 487–493, 1989.

General descriptions of the protein are described in the following reference:

5) N. Mukaida et al., Microbiol. Immunol. 36, 773–789, 1992.

MCP-1 and GDCF described in the References 3) and 4) are the same substance as MCAF, described in the References 1) and 2).

It is known that MCAF strongly attracts and activates monocytes, and uses exploiting immunopotentiation and anti-tumor properties are suggested in the above-mentioned references. Further, as a general concept, it is known that monocytes which have gathered in a wound play a role in the natural healing of the wound. However, it is not known that MCAF has an activity to directly promote therapy of wounds.

It is known that several proteinous growth factors promote healing of wounds. For example, growth factors such as fibroblast growth factor (FGF), epidermal growth factor (EGF), transforming growth factor (TGF-α, TGF-β), platelet-derived growth factor (PDGF), endothelial cell growth factor (ECGF) and keratinocyte growth factor are expected to have therapeutic activities for wounds (Reference 6).

6) T. A. Mastoe et al., J. Clin. Invest., 87, 694–703 (1991)

It was recently reported in U.S. Pat. No. 5,202,118 that interleukin-1 (IL-1) has a therapeutic effect for wounds.

DISCLOSURE OF THE INVENTION

An object of the present invention is to provide a therapeutic agent for treating wounds, which does not employ the growth factors or proteins inducing growth factors, but has properties and actions totally different from these substances, and which has a strong therapeutic effect.

That is, the present invention provides a therapeutic agent for treating wounds comprising as an effective ingredient MCAF or a variant thereof having a monocyte-chemotactic activity or a derivative of MCAF or said variation thereof.

By the present invention, a useful therapeutic agent which promotes healing of wounds such as traumatic ulcers caused by burn, trauma, surgery and the like, and basic disorder ulcers caused by endogenous factors (digestive fluid) and the like was provided.

BEST MODE FOR CARRYING OUT THE INVENTION

Figure 1:
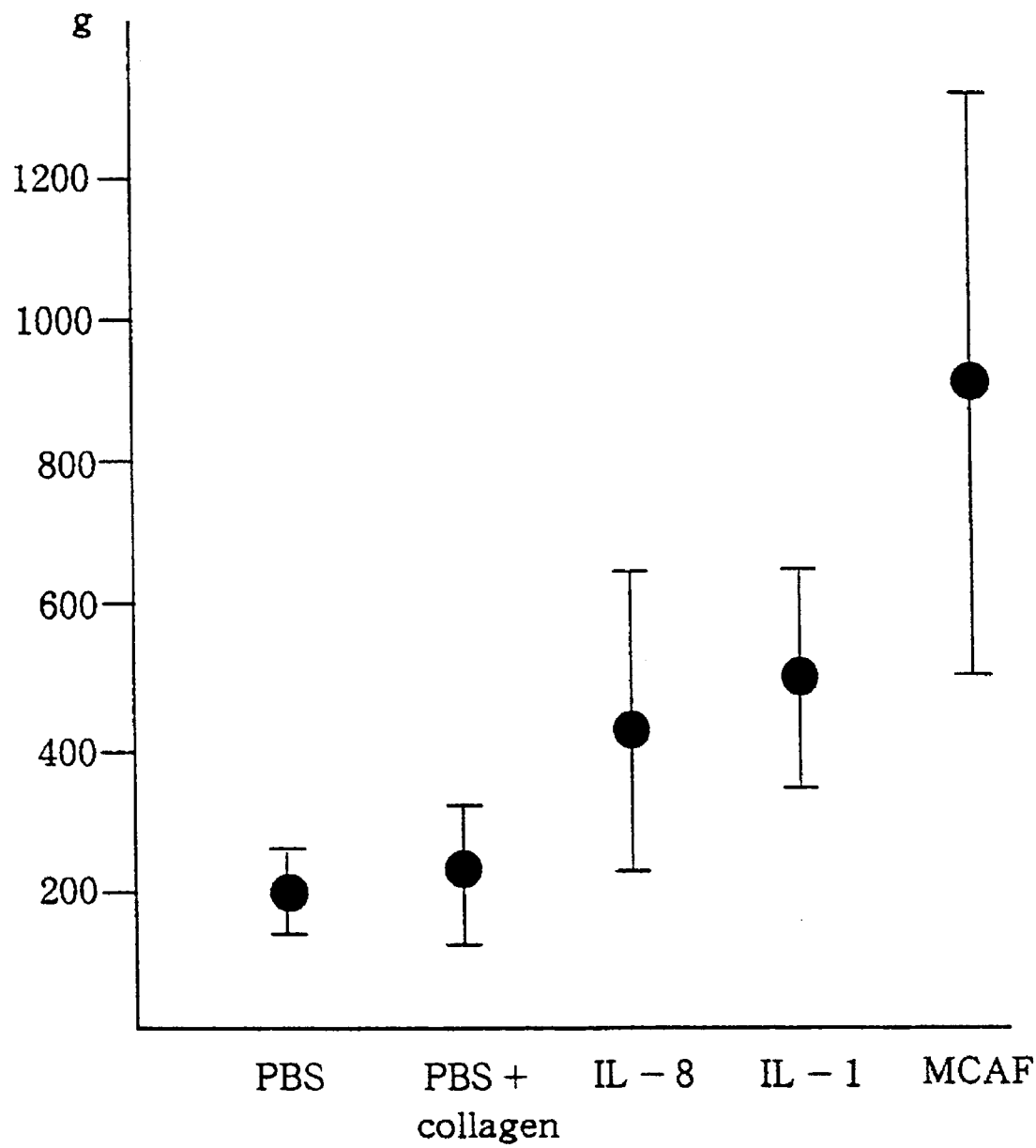
FIG. 1 shows tensile strengths of skin samples at 7 days after wounding.

MCAF is a protein consisting of 76 amino acids, which attracts and activates monocytes, as described in the above-mentioned References 1) to 5). The amino acid sequence of MCAF is shown in SEQ ID NO. 1 in the Sequence Listing.

In the present invention, variants of MCAF, which substantially have the amino acid sequence of MCAF, and which attract and activate monocytes can also be used as the effective ingredient. Here, the term "variants of MCAF" means that it substantially has the amino acid sequence of MCAF, and the term includes those compounds in which amino acids in the amino acid sequence of MCAF are naturally or artificially deleted, added or substituted to the extent that the monocyte-attracting property of MCAF is not lost. Sequences in the N-terminal and C-terminal regions of naturally occurring and recombinant MCAF may vary (increase or decrease in amino acid residues) depending on the production conditions and these are included in the scope of the present invention. Further, in the present invention, derivatives obtained by chemically or biochemically modifying MCAF or the above-mentioned MCAF variants (e.g., those obtained by chemically linking polyethylene glycol or an analogue thereof; those obtained by attaching phosphate or sulfate groups; those treated with a peptidase such as an endopeptidase; those treated with a sugar chain-modifying enzyme or a sugar chain-attaching enzyme, such as sialidase) may also be used as the effective ingredient. Analogues of MCAF having the number of amino acids and arrangement of cysteine residues, which are similar to those in MCAF, are known. In human, RANTES, MCP-2, MCP-3, LD78, ACT2 and I-309 are known, and in mouse, JE, MIP-1α, MIP-β, TCA-3 and the like are known as structural analogues of MCAF (above-described References 4) and 5)). Recently, MCP-2 and MCP-3 were reported as MCAF analogues (Reference 6: J. Van Damme et al., J. Exp. Med., 176, 59–65, 1992)). Among these, those which attract or activate monocytes or macrophages are included in the variants of MCAF in the present invention and may be used as an effective ingredient of the therapeutic agent for treating wounds according to the present invention. In particular, since it has been reported that RANTES, MCP-2, MCP-3 and JE attract monocytes and macrophages (the above-mentioned References 5) and 6)), these substances and variants thereof, as well as their derivatives can be used as an effective ingredient in the therapeutic agent for treating wounds according to the present invention.

The process for producing MCAF is not restricted and MCAF produced by known methods may be suitably employed. For example, purified MCAF may be obtained by ligating the cDNA described in the above-mentioned Reference 2) or 4) downstream of an appropriate regulatory region such as the promoter of SV40 or cytomegalovirus, a promoter of baculovirus, a promoter of amino acid-synthesizing and metabolizing gene, a promoter of sugar-synthesizing and metabolizing gene or the like to obtain an expression vector; introducing the expression vector into animal cells, insect cells, eukaryotic unicellular organisms, prokaryotic cells or the like to make the cells produce MCAF; and purifying the produced MCAF by appropriately combining column chromatographies such as affinity chromatography, ion-exchange chromatography, hydrophobic chromatography and chromatography utilizing antibody-bound carrier. A number of methods for producing a substance by genetic engineering process are known and MCAF can be produced by combining the known processes.

Alternatively, cells which intrinsically produce MCAF or which produce MCAF upon some stimulation, such as monocytes, fibroblasts, endothelial cells, keratinocytes, smooth muscle cells, astrocytes, or cell lines such as THP-1 (myelomonocyte) and U-105MG (glioma) are cultured so as to make the cells produce MCAF with or without appropriate stimulation; and MCAF may then be purified by the above-mentioned purification method. MCAF-producing cells and the conditions for stimulating the cells are described in the above-mentioned References 4) and 5).

Human MCAF having the amino acid sequence shown in SEQ ID NO. 1 in the Sequence Listing is commercially available (see Example 1 below), and such a commercially available MCAF may suitably be employed in the present invention.

The term "wound" herein means damages of tissues including skin and mucous membrane, and includes skin ulcers. Skin ulcers include traumatic ulcers caused by burn, trauma or surgery; circulatory disorder ulcers such as decubitus, cnemial ulcers and the like; and basic disorder ulcers such as skin diseases, and endogenous (digestive fluid) ulcers. In the examples, the effectiveness of the present invention is clearly shown using a skin wound model of rabbits. From the prominent effectiveness in curing wounds shown in the examples, the therapeutic effect of MCAF for curing skin ulcers, especially traumatic ulcers is easily expected.

To treat the wounds, which is an object of the present invention, a composition comprising MCAF or a variant thereof having a monocyte-attracting property or a derivative of MCAF or a variant thereof in a pharmaceutically acceptable carrier is administered to the body. The wounds to which the composition is administered are, as mentioned above, damages of tissues including skin and mucous membrane, and include skin ulcers such as traumatic ulcers caused by burn, trauma or surgery; circulatory disorder ulcers such as decubitus, cnemial ulcers and the like; and basic disorder ulcers such as skin diseases, and endogenous (digestive fluid) ulcers.

Other components to be blended may be water, organic solvents or other general pharmaceutically acceptable additives. Needless to say, however, the object of the present invention may also be attained without an additive. Examples of the pharmaceutically acceptable additives include collagen, heparin, polyvinyl alcohol, polyvinylpyrrolidone, carboxyvinyl polymer, sodium carboxymethyl cellulose, sodium polyacrylate, sodium alginate, hyaluronic acid, water-soluble dextran, sodium carboxymethyl starch, pectin, methyl cellulose, ethyl cellulose, xanthane gum, gum arabi, casein, gelatin, agar, polyethylene glycol, diglycerin, glycerin, propylene glycol, polyethylene glycol, vaseline, paraffin, stearyl alcohol, stearic acid, human serum albumin (HSA), mannitol, sorbitol, lactose and pharmaceutically acceptable surfactants. The additives may be appropriately selected depending on the formulation of the therapeutic agent of the present invention from the above-mentioned additives and combinations thereof, but, needless to say, the additives are not restricted to those mentioned above.

According to the present invention, other drugs, biological formulations and synthetic pharmaceuticals may be simultaneously or sequentially administered together with MCAF. The other drugs may be those having anti-inflammatory activities, peripheral circulation-improving activities, thrombus formation-inhibiting activities, tissue-repairing activities; those known to have therapeutic effects for treating alimentary canal ulcers; heparin; or therapeutic agents for treating wounds which reinforce or supplement the effects of the present invention.

Although the method of administration is not restricted, in view of the object of the present invention, topical administration is preferred. Formulations for topical administration include external formulations, suppositories and injection solutions. When treating alimentary canal ulcers, oral administration can be appropriately selected. External formulations include application formulations such as ointments, gels, creams, emulsions and lotions; pasting formulations such as tapes and patches; sprays; and powders. Administration dose of the effective ingredient may be selected from the range of 0.001 µg to 100 mg per wound per day, preferably 0.01 µg to 1 mg per wound per day. However, the administration dose varies depending on the size and state of the wound and so the administration dose is not restricted to the range mentioned above. When used as an external formulation, the content of the effective ingredient in the formulation may be 0.000001% by weight to 10% by weight, preferably 0.00001% by weight to 0.1% by weight. The times of administration may be once when wounded, or one to several times per day, or once per two or several days, although not restricted thereto.

EXAMPLES

The present invention will now be described in more detail and more concretely by way of examples. Needless to say, however, the present invention is not restricted by the examples.

Example 1

Effect of MCAF on Wounds of Rabbits
1) Testing Method

As the rabbits, NZW (New Zealand White) rabbits were employed, and each group consisted 4 rabbits.

After anesthetizing each rabbit with 75 mg of pentobarbital, five incised wounds having a length of 5 cm were formed in the back of each rabbit. As MCAF, human MCAF prepared by genetic recombination, which is commercially available from Pepro tech, Inc., Rocky Hill, N.J. 08553, USA was used.

The compositions described below (drug and control drugs) were topically injected. 0.1 ml of the composition was injected per each injection, and totally 1 ml of the composition was injected per wound.

(1) PBS (1 ml)

(2) PBS (1 ml)+bovine collagen (1 mg)

(3) PBS (1 ml)+bovine collagen (1 mg)+IL-8 (5 µg)

(4) PBS (1 ml)+bovine collagen (1 mg)+IL-1 (5 µg)

(5) PBS (1 ml)+bovine collagen (1 mg)+MCAF (5 µg)

Rabbits were sacrificed 7 days or 14 days after the injection. The entire skin of the back of each rabbit was peeled off and samples in the form of a tape having a width of 1.5 cm, containing the incised wound at a right angle to the tape were prepared. The tensile strengths of the tapes were measured. The tensile strength was measured by using Autograph Tension Tester commercially available from Shimazu Seisakusho, in accordance with the method described in Watanabe, Y. et al., Surg. Res. Comm., 10, 267–277, 1991.

2) Test Results

Figure 2:
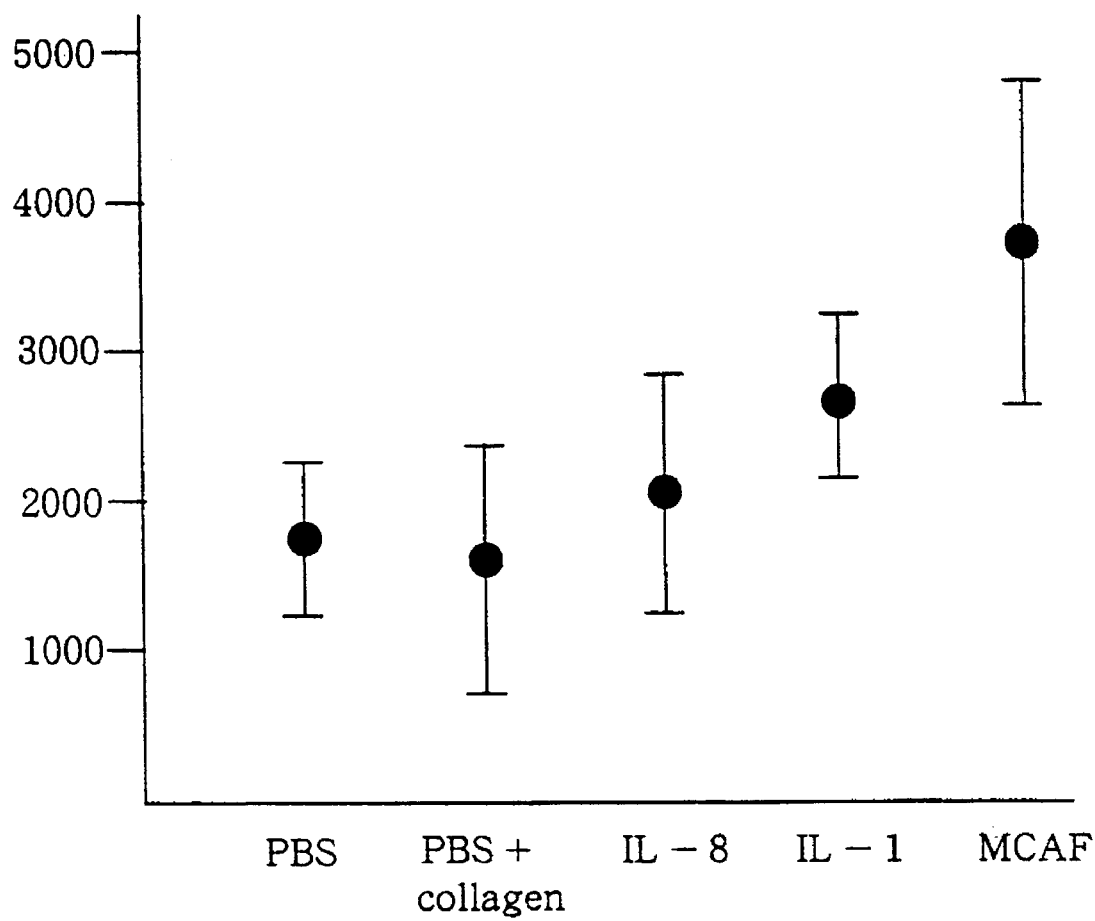
FIG. 2 shows tensile strengths of skin samples at 14 days after wounding.

The results obtained 7 days after the injection are shown in Table 1 and FIG. 1, and the results obtained 14 days after the injection are shown in Table 2 and FIG. 2.

hydrophobic chromatography, cation-exchange chromatography and reverse phase HPLC, was employed. This MCAF

TABLE 1

Tensile Strength of Wounded Skin at 7 Days after Wounding

| Administered Composition | Measured Tensile Strength (grams) | | | | | |
|---|---|---|---|---|---|---|
| | Rabbit 1 | Rabbit 2 | Rabbit 3 | Rabbit 4 | Average | SD |
| PBS | 205 | 250 | 130 | 405 | 248 | 116 |
| PBS + bovine collagen | 165 | 220 | 105 | 440 | 233 | 146 |
| PBS + bovine collagen + IL-8 | 345 | 485 | 165 | 760 | 439 | 251 |
| PBS + bovine collagen + IL-1 | 590 | 590 | 250 | 565 | 498 | 166 |
| PBS + bovine collagen + MCAF | 685 | 1225 | 320 | 1395 | 906 | 494 |

TABLE 2

Tensile Strength of Wounded Skin at 14 Days after Wounding

| Administered Composition | Measured Tensile Strength (grams) | | | | | |
|---|---|---|---|---|---|---|
| | Rabbit 5 | Rabbit 6 | Rabbit 7 | Rabbit 8 | Average | SD |
| PBS | 2250 | 2300 | 1060 | 1480 | 1772 | 605 |
| PBS + bovine collagen | 1170 | 2900 | 2560 | 704 | 1584 | 945 |
| PBS + bovine collagen + IL-8 | 3275 | 1925 | 1470 | 1428 | 2025 | 864 |
| PBS + bovine collagen + IL-1 | 3310 | 3225 | 2350 | 1960 | 2711 | 663 |
| PBS + bovine collagen + MCAF | 4370 | 4000 | 4650 | 1900 | 3730 | 1249 |

Table 1 shows the measured tensile strengths of the skin samples 7 days after the injection and Table 2 shows the measured tensile strengths of the skin samples 7 days after the injection in terms of grams. Each of the 4 values shown as the actually measured values correspond to each of the 4 rabbits from the left column. The average and standard deviation (SD) are shown in the right columns.

From Table 1, FIG. 1, Table 2 and FIG. 2, an increase in the tensile strength is clearly shown in those samples to which MCAF was administered. Thus, it is concluded that MCAF is effective as a therapeutic agent for treating wounds. A statistical analysis (Student's t test) was performed on Table 1. The group to which MCAF was administered, that is, the group to which composition (5) was administered, showed significant difference with a significance probability of not more than 0.05 with respect to the group to which PBS alone was administered, that is, the group to which composition (1) was administered, and with respect to the group to which collagen was administered, that is, the group to which composition (2) was administered. Although no significant differences were observed among other values and among the values in Table 2 in this statistical analysis because of the limited number of the animals, by precisely comparing the measured value of each rabbit in Tables 1 and 2, an increase in the tensile strength is clearly observed in the group to which MCAF was administered.

Example 2

The therapeutic effects of MCAF for skin wounds were compared with those of other growth factors. Further, dose dependence of the therapeutic effects of MCAF was examined.

1) Testing Method

The following experiments were carried out in accordance with the method in Example 1 in principle.

As the MCAF, one obtained from human fibroblast cells stimulated by polyI:polyC 50 mg/l which was purified by exhibited the same physiological actions as the MCAF commercially available from Pepro tech, Inc.

NZW female rabbits (body weight: 2.5–3.5 kg) were used. Anesthesia was performed by administering 25 mg/kg of pentobarbital. The length of the incised wounds in the skin of the back was 6 cm. The wounds were closed by surgical staples at 1.5 cm intervals. MCAF or other growth factors were formulated into phosphate buffer containing 10 mg/ml of emulsified collagen (Zyderm Collagen Corp., Palo Alto, Calif.). When closing the wounds by staples, 0.5 ml of the above-mentioned emulsion was administered per each wound. Seven days after the administration, rabbits were sacrificed and skin samples in the form of a tape having a width of 1.5 cm, each of which contains the wound at its center at right angles to the tape, were prepared. Two micrograms of EGF (recombinant human epidermal growth factor) commercially available from Becton Dickinson, 2 μg of EGF (recombinant human basic fibroblast growth factor) commercially available from Genzoyme, 2 μg of TGF-α (recombinant human transforming growth factor-α) commercially available from Becton Dickinson or 2 μg of TGF-β (human transforming growth factor) commercially available from Becton Dickinson was applied to each wound.

In the test for examining the dose dependence of the therapeutic effect of MCAF, the administration dose of MCAF per wound was 0.2, 1.0 or 5.0 μg.

Figure 3:
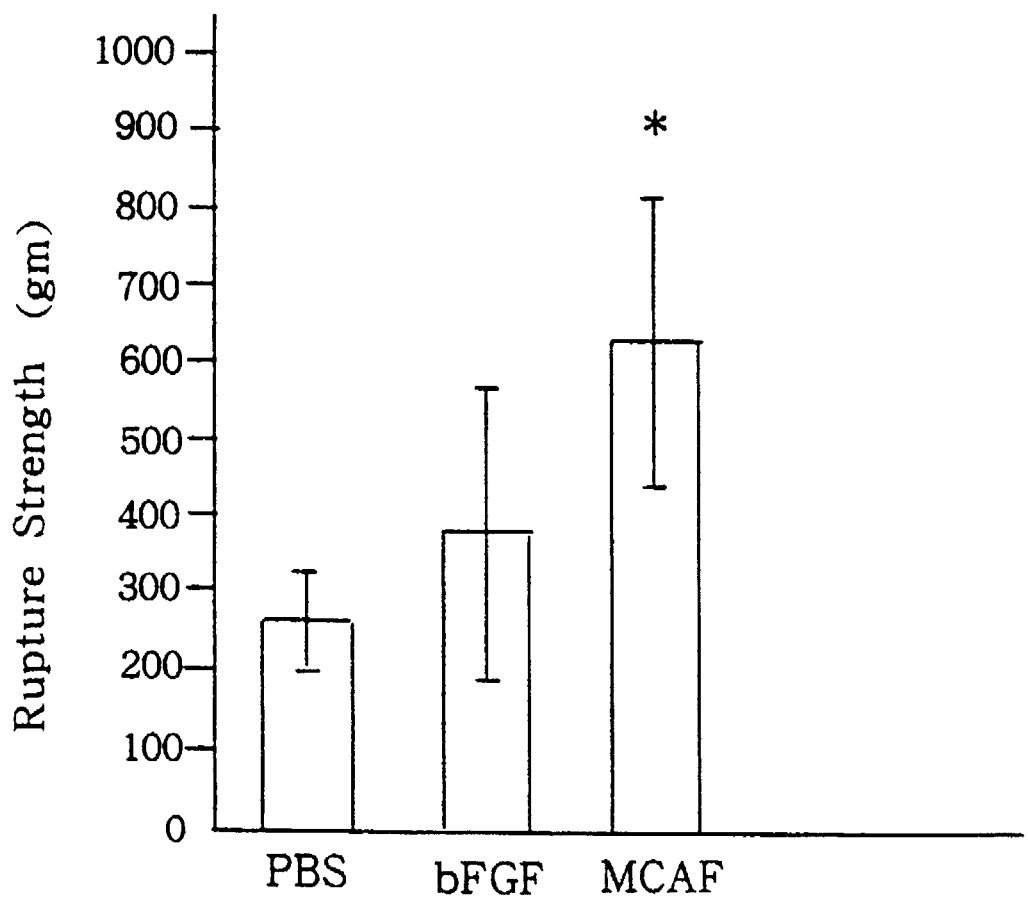
FIG. 3 shows therapeutic effects of MCAF for wounds in comparison with those by other growth factors.
Figure 4:
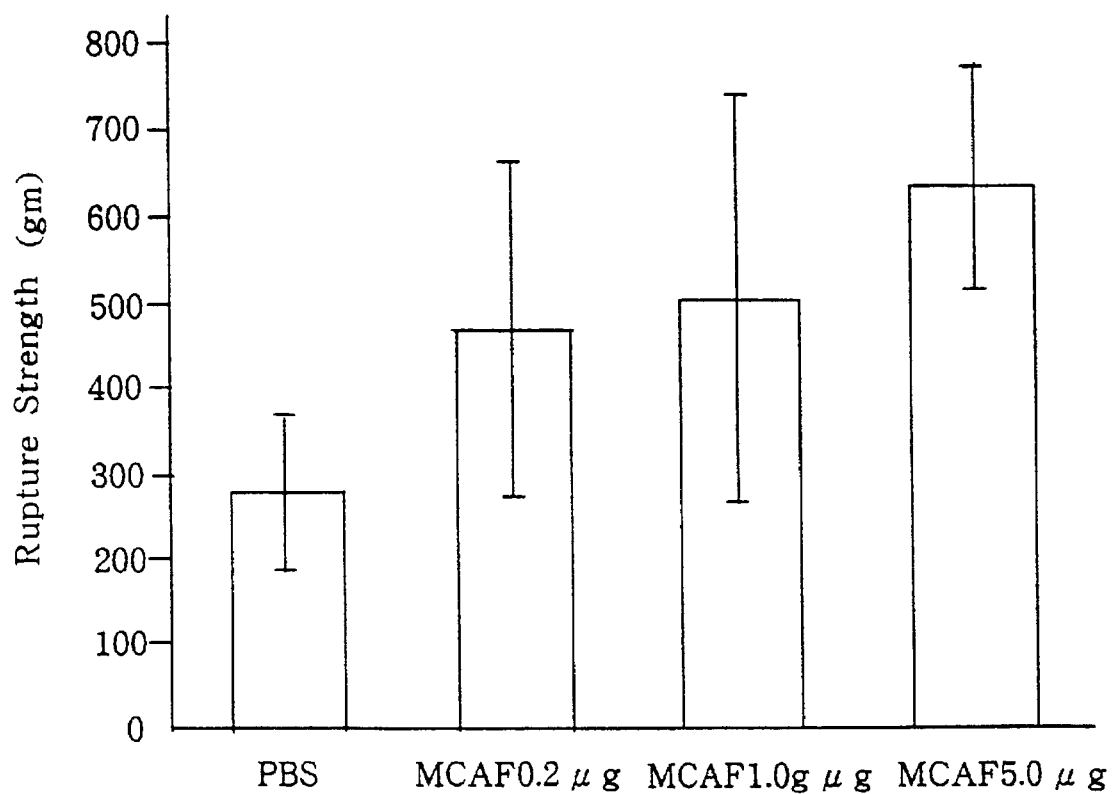
FIG. 4 shows therapeutic effects of MCAF for wounds.

In all cases, the skin samples were tested for their tensile strengths in the same manner as in Example 1 and the results are shown in terms of gm (gram). The results are shown in FIGS. 3 and 4. The results are shown in terms of average ±SD (standard deviation) and statistical analysis (Student's t test) was performed.

In addition to the tensile strength test, each skin sample was stained with hematoxylin-eosin after being fixed by formalin, and granulation at the sutured regions was observed.

2) Results

Comparison among the effects by MCAF and by other growth factors are shown in FIG. 3. The rupture strength was 267.5±59.6 grams when PBS alone was administered, 385.4±189.9 grams when bFGF was administered, and 645.0 ±188.8 grams when MCAF was administered. The results of the group to which MCAF was administered were significant with respect to the group to which PBS alone was administered with p<0.05. Further, MCAF was more effective than bFGF. By microscopic examination, no pathological abnormalities were observed in any case.

The dose dependence of the effects of MCAF is shown in FIG. 4. The rupture strength was 275.1±90.5 grams when PBS alone was administered, 471.0±193.3 grams when 0.2 μg of MCAF was administered, 504.6±23.7 grams when 1.0 μg of MCAF was administered and 644.0±128.2 grams when 5.0 μg of MCAF was administered. Differences between pathological observations depending on the dose of MCAF were not observed.

INDUSTRIAL AVAILABILITY

As described above, the therapeutic agent for treating wounds according to the present invention exhibits excellent therapeutic effect for wounds. Therefore, it is expected that the therapeutic agent for treating wounds according to the present invention will very much contribute to therapy of wounds in the medical field.

SEQUENCE LISTING

SEQ ID NO.: 1

SEQUENCE LENGTH: 76

SEQUENCE TYPE: amino acid

SEQUENCE DESCRIPTION

| Gln | Pro | Asp | Ala | Ile | Asn | Ala | Pro | Val | Thr | Cys | Cys | Tyr | Asn | Phe | Thr |
|1||||5|||||10|||||15||

| Asn | Arg | Lys | Ile | Ser | Val | Gln | Arg | Leu | Ala | Ser | Tyr | Arg | Arg | Ile | Thr |
||||20||||25|||||30|||

| Ser | Ser | Lys | Cys | Pro | Lys | Glu | Ala | Val | Ile | Phe | Lys | Thr | Ile | Val | Ala |
|||35|||||40||||45||||

| Lys | Glu | Ile | Cys | Ala | Asp | Pro | Lys | Gln | Lys | Trp | Val | Gln | Asp | Ser | Met |
||50||||55||||60||||

| Asp | His | Leu | Asp | Lys | Gln | Thr | Gln | Thr | Pro | Lys | Thr |
|65||||70|||||75||

We claim:

1. A method of treating wounds comprising administering to a patient in need thereof an effective amount of a therapeutic agent having as an active ingredient a compound selected from the group consisting of monocyte chemotactic and activating factor, a variant thereof having monocyte attracting properties, a derivative of monocyte chemotactic and activating factor and a variant of said derivative.

2. A method of claim 1 wherein said therapeutic agent is administered in a form selected from the group consisting of external formulations, suppositories, injections and orally.

3. A method of claim 1 wherein said active ingredient is administered in a range of 0.001 μg to 100 mg per wound per day.

4. A method of claim 1 wherein said therapeutic agent is administered one to several times per day.

5. A method of claim 1 wherein said wound is selected from the group consisting of damaged tissues; skin ulcers caused by burns, trauma or surgery; circulatory disorder ulcers; skin diseases; and digestive fluid ulcers.

6. The method of claim 1, wherein said variant thereof is obtained by the deletion, substitution, or addition of amino acid residues of MCAF.

7. The method of claim 1, wherein said derivative thereof is obtained by biochemical modification of MCAF, wherein said modification is selected from the group consisting of chemical linking with polyethylene glycol, phosphate group attachment, sulfate group attachment, peptidase treatment, treatment with a sugar chain-modifying enzyme, and treatment with a sugar attachment enzyme.

8. The method of claim 1, wherein said variant thereof is selected from the group consisting of RANTES, MCP-2, MCP-3, LD78, ACT2, I-309, JE, MIP-1α, MIP-1β, and TCA.

9. The method of claim 6, wherein said variant is obtained by deletion or addition of amino acid residues from the amino terminal end of MCAF.

10. The method of claim 6, wherein said variant is obtained by deletion or addition of amino acid residues from the carboxy terminal end of MCAF.

* * * * *